United States Patent
Ferreira

(10) Patent No.: US 10,286,087 B2
(45) Date of Patent: May 14, 2019

(54) IMMUNOADSORPTION

(71) Applicant: uniQure IP B.V., Amsterdam (NL)

(72) Inventor: Valerie Ferreira, Amsterdam (NL)

(73) Assignee: UNIQURE IP B.V., Amsterdam (NL)

( * ) Notice: Subject to any disclaimer, the term of this patent is extended or adjusted under 35 U.S.C. 154(b) by 0 days.

(21) Appl. No.: 15/843,803

(22) Filed: Dec. 15, 2017

(65) Prior Publication Data

US 2018/0169273 A1 Jun. 21, 2018

(30) Foreign Application Priority Data

Dec. 16, 2016 (EP) ..................................... 16204806

(51) Int. Cl.
| | | |
|---|---|---|
| *A61K 48/00* | (2006.01) | |
| *A61K 9/00* | (2006.01) | |
| *C12N 7/00* | (2006.01) | |
| *A61M 1/36* | (2006.01) | |
| *C12N 15/86* | (2006.01) | |
| *A61M 1/34* | (2006.01) | |
| *A61M 5/14* | (2006.01) | |

(52) U.S. Cl.
CPC ........ *A61K 48/0083* (2013.01); *A61K 9/0019* (2013.01); *A61K 48/0075* (2013.01); *A61M 1/3486* (2014.02); *A61M 1/362* (2014.02); *A61M 1/3679* (2013.01); *A61M 5/14* (2013.01); *C12N 7/00* (2013.01); *C12N 15/86* (2013.01); *A61M 2202/0417* (2013.01); *C12N 2750/14143* (2013.01)

(58) Field of Classification Search
None
See application file for complete search history.

(56) References Cited

U.S. PATENT DOCUMENTS 6,406,861 B1 * 6/2002 Henderson ............. A61K 48/00
424/131.1
9,114,161 B2 * 8/2015 Barkats ............. A61K 48/0075

FOREIGN PATENT DOCUMENTS

WO WO-01/17537 A2 3/2001
WO WO-01/17537 A3 3/2001

OTHER PUBLICATIONS

Eming & Hertl (2006) "Immunosorption in pemphigus", Autoimmunity, 39(7): 609-16.*
Ikonomov, et al. (1992) "Adsorption profile of commercially available adsorbents: an in vitro evaluation", The International Journal of Artificial Organs, 15(5): 312-19 (Abstract Only).*
Taniguchi, et al. (1996) "In vivo immunoadsorption of antipig antibodies in baboons using a specific Gal(alpha)1-3Gal column", Transplantation, 62(10): 1379-84.*
Batra, et al. (1999) "Adenoviral Gene Transfer is Inhibited by Soluble Factors in Malignant Pleural Effusions", American Journal of Respiratory Cell and Molecular Biology, 22: 613-19.*
Madsen, et al. (2009) "Adeno-associated virus serotype 2 induces cell-mediated immune responses directed against multiple epitopes of the capsid protein VP1", Journal of General Virology, 90: 2622-33.*
Chen et al., "Pre-existent adenovirus antibody inhibits systemic toxicity and antitumor activity of CN706 in the nude mouse LNCaP xenograft model: implications and proposals for human therapy", Human Gene Therapy, 2000, vol. 11, pp. 1553-1567.
Chicoine et al., "Plasmapheresis eliminates the negative impact of AAV antibodies on microdystrophin gene expression following vascular delivery", Molecular Therapy, 2014, vol. 22, No. 2, pp. 338-347.
Extended European Search Report issued in EP 16204806.0, dated May 24, 2017.
Rahman et al., "Specific depletion of human anti-adenovirus antibodies facilitates transduction in an in vivo model for systemic gene therapy", Molecular Therapy, 2001, vol. 3, No. 5, pp. 768-778.

* cited by examiner

*Primary Examiner* — Robert M Kelly
(74) *Attorney, Agent, or Firm* — Sunit Talapatra; Foley & Lardner LLP

(57) ABSTRACT

Upon administration of rAAV vectors the humoral immune response (neutralizing antibodies) is the first barrier that needs to be overcome. Surprisingly it was found that by using immunoadsorption for depletion of immunoglobulins from the blood (plasma), subjects can be highly efficiently treated with rAAV vectors, i.e. obtain highly efficient transduction after rAAV vector administration, in spite of the presence of high levels of nAb.

16 Claims, 5 Drawing Sheets

IMMUNOADSORPTION

CROSS-REFERENCE TO RELATED APPLICATIONS

The present non-provisional U.S. Patent Application claims priority to European Patent Application No. 16204806.0, filed Dec. 16, 2016, the entire disclosure of which is incorporated herein by reference.

FIELD OF THE INVENTION

The invention relates to the field of recombinant adeno-associated viral (rAAV) vector based gene therapy. In particular, to neutralizing antibodies (immunoglobulins) (nAb) against rAAV in subjects and to the use of immunoadsorption for depleting immunoglobulins from the blood prior to rAAV administration.

BACKGROUND OF THE INVENTION

Recombinant adeno-associated virus (rAAV) vectors show great promise for gene therapy in a variety of different genetic disorders. AAV vectors have an excellent safety profile, as demonstrated in non-clinical and clinical studies. Furthermore, AAV vectors were shown to mediate a stable therapeutic transgene expression in several non-clinical studies, and more recently in clinical studies. AAV vectors have been successful in phase I/II studies for haemophilia B, cystic fibrosis, alpha-1 anti-trypsin deficiency, Parkinson disease, Duchenne muscular dystrophy and Leber's congenital amaurosis (Selot et al., Current Pharmaceutical Biotechnology, 2013, 14, 1072-1082). Alipogene tiparvovec (Glybera®, uniQure) has been granted marketing authorization in Europe as a gene therapy for the treatment of lipoprotein lipase deficiency (LPLD). Hence rAAV vectors are the gene transfer vectors of choice for the delivery of genes in humans in vivo.

One major challenge for a successful administration of AAV vector is the presence of neutralizing antibodies (immunoglobulins) (nAb) that have developed following exposure to wild-type AAV or AAV-based vectors. In both cases, the neutralizing serotype-specific antibodies directed towards the viral capsid proteins reduce the efficiency of gene transfer with AAV of the same serotype.

The current practice in the clinic with regard to pre-existing immunity involves the screening of patients for exclusion should patients have neutralizing antibodies against the AAV capsid (Brimble et al. Expert Opin Biol Ther 2016, 16(1):79-92 and Boutin et al. Hum Gene Ther 2010, 21:704-712). Immunosupressive regimens have been tried in order to reduce the formation of nAb upon first administration to allow for a second administration (Corti et al., Mol Ther—Meth Clin Dev (2014) 1, 14033; Mingozzi et al. Mol Ther vol. 20 no. 7, 1410-1416; McIntosh et al. Gene Ther 2012, 19, 78-85)).

Furthermore, strategies have been suggested to overcome pre-existing antibodies which include plasma exchange and the use of immunosuppressive regimens. Plasma exchange strategies involve the removal of plasma from the blood and exchanging it for plasma not containing neutralizing antibodies (e.g. from a donor or the subject itself) or a defined replacement fluid (Chicoine et al., Mol Ther 2014, vol. 22 no. 2 338-347; Hurlbut et al. Mol Ther 2010, vol. 18 no. 11 1983-1984). Immunosuppressive regimens aimed at reducing nAb include rituximab combined with Cyclosporin A (Mingozzi et al. Mol Ther vol. 20 no. 7, 1410-1416). Such strategies have been tested in animal models obtaining limited success, being somewhat effective in subjects having low nAb titers. In view of these results it has been suggested to combine different strategies and/or use a higher rAAV vector dose (tenfold) in order to overcome pre-existing antibodies and achieve effective transduction of e.g. the liver (Hurlbut et al. Mol Ther 2010, vol. 18 no. 11 1983-1984; Mingozzi et al. Mol Ther vol. 20 no. 7, 1410-1416).

Hence, there is a need in the art for strategies that allow administration of rAAV vectors in subjects that have, or may be suspected to have, neutralizing antibodies.

BRIEF DESCRIPTION OF THE INVENTION

Upon administration of rAAV vectors the humoral immune response, i.e. neutralizing antibodies, is the first barrier that needs to be overcome. The second barrier that needs to be overcome is the cellular response, i.e. once rAAV has been delivered to the target cell transduced cells may be eliminated because these present antigens derived from the rAAV capsid protein and/or the expressed transgene. The second barrier, i.e. the cellular response to AAV capsids, is transient in nature and may be controlled by monitoring subjects that have underwent rAAV gene therapy treatment and/or by immunosuppressive treatments. As outlined above, strategies that have been employed that are aimed at overcoming the first barrier which included the use of plasma exchange and/or pharmaceutical interventions. Strategies employed were cumbersome and had limited success. The current inventors now provide for a new and improved means of avoiding this first barrier. Surprisingly it was found that by using immunoadsorption for depletion of immunoglobulins from the blood (plasma), subjects can be highly efficiently treated with rAAV vectors, i.e. obtain highly efficient transduction after rAAV vector administration, in spite of these subjects having initially high levels of nAb. By said immunoadsorption, a therapeutic window is provided that transiently reduces nAb levels long enough to allow rAAV delivery to the target cells without severe risks for the subject being treated. This is because immunoadsorption is a relatively mild treatment especially when compared with proposed and tested prior art methods. Also, the cellular response can depend on the dose of rAAV being administered. Without being bound by theory, because the dose of rAAV that needs to be administered can be lower to achieve efficient levels of transduction by the invention, not only the first barrier of the humoral response may be overcome, but it may also contribute to reducing or even avoiding the second barrier.

Hence, according to the invention, such immunoadsorption methods can either involve non-specific or specific removal of neutralizing rAAV immunoglobulins and such immunoadsorption methods are employed outside of the body, i.e. extracorporeal. Accordingly, in a first embodiment an rAAV vector is provided for use in the treatment of a subject, wherein said subject has been subjected to extracorporeal depletion of immunoglobulins using immunoadsorption prior to administration of said rAAV vector.

Also, methods are provided for reducing the anti-rAAV immunoglobulin concentration in the blood, comprising the steps of:
  a) providing blood;
  b) providing a device for immunoadsorption;
  c) separating the blood provided in a) in plasma components and cellular components;
  d) subjecting the plasma components obtained in c) to immunoadsorption by using the device provided in b);

e) reconstituting the blood by combining the cellular components obtained in c) with the plasma components subjected to immunoadsorption obtained in d).

Preferably, said reconstituted blood is to be administered to a subject such that the blood of the subject has a reduced anti-rAAV immunoglobulin concentration in the blood. Subsequently, said subject can have rAAV administered.

DEFINITIONS

An "rAAV vector" refers to a recombinant adeno-associated virus (AAV) vector which is derived from the wild type AAV by using molecular methods. An rAAV vector is distinguished from a wild type (wt)AAV vector, since at least a part of the viral genome has been replaced with a transgene, which is a non-native nucleic acid with respect to the AAV nucleic acid sequence as further defined herein. Wild type AAV belongs to the genus *Dependovirus*, which in turn belongs to the subfamily of the Parvovirinae, also referred to as parvoviruses, which are capable of infecting vertebrates. Parvovirinae belong to family of small DNA animal viruses, i.e. the Parvoviridae family. As may be deduced from the name of their genus, members of the *Dependovirus* are unique in that they usually require coinfection with a helper virus such as adenovirus or herpes virus for productive infection in cell culture. The genus *Dependovirus* includes AAV, which normally infects humans (e.g., serotypes 1, 2, 3A, 3B, 4, 5, 6, 7, 8, 9, 10, 11, 12, 13) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid or protein shell. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wtAAV infection in mammalian cells the Rep genes (i.e. Rep78 and Rep52) are expressed from the P5 promoter and the P19 promoter, respectively and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. wtAAV infection in mammalian cells relies for the capsid proteins production on a combination of alternate usage of two splice acceptor sites and the suboptimal utilization of an ACG initiation codon for VP2.

An rAAV vector may have one or preferably all wild type AAV genes deleted, but may still comprise functional ITR nucleic acid sequences. Preferably, the rAAV vector does not comprise any nucleotide sequences encoding viral proteins, such as the rep (replication) or cap (capsid) genes of AAV. At least one functional ITR sequence is necessary for the replication, rescue and packaging of vector genomes into AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be transduced or target cell. Typically, the inverted terminal repeats of the wild type AAV genome are retained in the rAAV vector. The ITRs can be cloned from the AAV viral genome or excised from a vector comprising the AAV ITRs. The ITR nucleotide sequences can be either ligated at either end to a transgene as defined herein using standard molecular biology techniques, or the wild type AAV sequence between the ITRs can be replaced with the desired nucleotide sequence. The rAAV vector preferably comprises at least the nucleotide sequences of the inverted terminal repeat regions (ITR) of one of the AAV serotypes, or nucleotide sequences substantially identical thereto, and at least one nucleotide sequence encoding a therapeutic protein (under control of a suitable regulatory element) inserted between the two ITRs. The majority of currently used rAAV vectors use the ITR sequences from AAV serotype 2. Preferred ITR sequences are ITRs from the AAV serotypes 2. A rAAV genome can comprise single stranded or double stranded (self-complementary) DNA. The single stranded nucleic acid molecule is either sense or antisense strand, as both polarities are equally capable of gene expression. Single stranded rAAV vectors may utilize the wild-type AAV ITR sequences, such as for example wild-type AAV2 ITR sequences, and double stranded (self-complementary) rAAV vectors may utilize a modified version of the ITRs, such as for example disclosed in International patent application with the publication number WO 01/92551. The rAAV vector may further comprise a marker or reporter gene, such as a gene for example encoding an antibiotic resistance gene, a fluorescent protein (e.g., gfp) or a gene encoding a chemically, enzymatically or otherwise detectable and/or selectable product (e.g., lacZ, aph, etc.) known in the art.

The rAAV vector, including all combinations of AAV serotype capsid and AAV genome ITRs, is produced using methods known in the art, as described in Pan et al. (J. of Virology (1999) 73: 3410-3417), Clark et al. (Human Gene Therapy (1999) 10: 1031-1039), Wang et al. (Methods Mol. Biol. (2011) 807: 361-404) and Grimm (Methods (2002) 28(2): 146-157), which are incorporated herein by reference. In short, the methods generally involve (a) the introduction of the rAAV genome construct into a host cell, (b) the introduction of an AAV helper construct into the host cell, wherein the helper construct comprises the viral functions missing from the wild type rAAV genome and (c) introducing a helper virus construct into the host cell. All functions for rAAV vector replication and packaging need to be present, to achieve replication and packaging of the rAAV genome into rAAV vectors. The introduction into the host cell can be carried out using standard molecular biology techniques and can be simultaneously or sequentially. Finally, the host cells are cultured to produce rAAV vectors and are purified using standard techniques such as CsCl gradients (Xiao et al. 1996, J. Virol. 70: 8098-8108). The purified rAAV vector is then ready for use in the methods. High titres of more than $10^{12}$ particles per ml and high purity (free of detectable helper and wild type viruses) can be achieved (Clark et al. supra and Flotte et al. 1995, Gene Ther. 2: 29-37). The total size of the transgene inserted into the rAAV vector between the ITR regions is generally smaller than 5 kilobases (kb) in size.

Alternatively, rAAV can be produced in a baculovirus system (BEVS). The initial baculovirus system for production of rAAV was described by Urabe et al (Urabe et al. [2002] Human Gene Therapy 13(16):1935-1943) and consists of three baculoviruses, namely Bac-Rep, Bac-cap and Bac-vec, co-infection of which into insect cells e.g. SF9 resulted in generation of rAAV. The properties of such produced rAAV, i.e. physical and molecular characteristic including potency, did not differ significantly from the rAAV generated in mammalian cells (Urabe [2002] supra). In order to accomplish efficient generation of rAAV vectors in insect cells the AAV proteins needed for the process had to be expressed at appropriate levels. This required a number of adaptations of operons encoding for Rep and Cap proteins. Wild type AAV expresses large Rep78 to small Rep52 from two distinct promoters p5 and p19 respectively and splicing of the two messengers results in generation of Rep68 and Rep52 variants. This operon organization results in limited expression of Rep78 and relatively higher expression of Rep52. In order to mimic the low 78 to 52 ratio Urabe and colleagues constructed a DNA cassette in which expression of Rep78 was driven by the partially deleted promoter for the immediate-early 1 gene (ΔIE-1) whereas Rep52 expression was controlled by a strong polyhedrin promoter (polh). The spliced variants of large and small Reps were not observed in insect cells which likely relates to the difference in splicing processes between mammalian and insect cells. Another technical challenge to be overcome was related to the expression of the three major viral proteins (VP's). Wild type AAV expresses VP1, 2 and 3 from p40 promoter. Arising messenger RNA is spliced into two species: one responsible for VP1 expression whereas the second expresses both VP2 and VP3 via a "leaky ribosomal scanning mechanism" where the protein is initiated from non-canonical start i.e. ACG, is occasionally missed by the ribosome complex which then proceeds further until it finds the canonical start of VP3. Due to the differences in splicing machinery between vertebrate and insect cells the above described mechanism did not result in generation of proper capsids in insect cells. Urabe et al., decided to introduce a modification of translational start of VP1 which was similar to these found in the VP2 in such a way that the translational start of VP1 was changed to ACG and the initiation context, which consists of 9 nucleotides preceeding VP1, was changed to those preceeding VP2. These genetic alterations resulted in expression of the three VPs in the correct stoichiometry that could properly assemble into capsids from a single polycistronic mRNA. The transgene cassette on the other hand was similar to what was previously described for mammalian based systems, flanked by ITRs as the only in trans required elements for replication and packaging. The initial baculovirus system by Urabe (2002, supra) has been further developed see e.g., Kohlbrenner et al. (2005) Molecular Therapy 12 (6):1217-1225; Urabe et al. (2006) Journal of Virology 80(4):1874-1885; WO 2007/046703; WO 2007/148971; WO 2009/014445 and WO 2009/104964.

The sequence encoding the capsid protein can be a capsid sequence as found in nature such as for example of AAV2, AAV5 and AAV8. Alternatively, the sequence can be man-made, for example, the sequence may be a hybrid form or may be codon optimized form, such as for example by codon usage of AcmNPv or *Spodoptera frugiperda*. For example, the capsid sequence may be composed of the VP2 and VP3 sequences of one serotype, such as for example AAV1, whereas the remainder of the VP1 sequence is of another serotype, such as for example AAV5. The man-made sequence may result of rational design or directed evolution experiments. This can include generation of capsid libraries via DNA shuffling, error prone PCR, bioinformatic rational design, site saturated mutagenesis. Resulting capsids are based on the existing serotypes but contain various amino acid or nucleotide changes that improve the features of such capsids. The resulting capsids can be a combination of various parts of existing serotypes, "shuffled capsids" or contain completely novel changes, i.e. additions, deletions or substitutions of one or more amino acids or nucleotides, organized in groups or spread over the whole length of gene or protein. See for example Schaffer and Maheshri; Proceedings of the 26th Annual International Conference of the IEEE EMBS San Francisco, Calif., USA to; Sep. 1-5, 2004, pages 3520-3523; Asuri et al. (2012) Molecular Therapy 20(2):329-3389; Lisowski et al. (2014) Nature 506(7488): 382-386, herein incorporated by reference.

In the context of the present invention a capsid protein shell may be of a different serotype than the rAAV vector genome ITR. An rAAV vector of the invention may thus be encapsidated by a capsid protein shell, i.e. the icosahedral capsid, which comprises capsid proteins (VP1, VP2, and/or VP3) of one AAV serotype, such as for example AAV serotype 5, whereas the ITRs sequences contained in that rAAV vector may be of another serotype, for example any of the rAAV serotypes described above, including a rAAV5 vector. In a preferred embodiment, an rAAV vector is encapsidated by a capsid protein shell of AAV serotype 5 or AAV serotype 2 or AAV serotype 8 wherein the rAAV genome or ITRs present in said rAAV vector are derived from AAV serotype 2 or AAV serotype 5 or AAV serotype 8. In this embodiment it is preferred that the rAAV vector is encapsidated by a capsid protein shell of the AAV serotype 5 and the rAAV genome or ITRs present in said vector are derived from AAV serotype 2. In another embodiment, it is preferred that the rAAV vector is encapsidated by a capsid protein shell of the AAV serotype 2 and the rAAV genome or ITRs present in said vector is derived from AAV serotype 2.

The complete genome of AAV5 and other AAV serotypes has been sequenced (Chiorini et al. 1999, J. of Virology Vol. 73, No. 2, p 1309-1319) and the nucleotide sequence is available in GenBank (Accession No. AF085716; 23 Feb. 2015). The ITR nucleotide sequences of AAV5 are thus readily available to a skilled person. The complete genome of AAV2 is available in NCBI (NCBI Reference Sequence NC_001401.2; 2 Dec. 2014). They can be either cloned or made by chemical synthesis as known in the art, using for example an oligonucleotide synthesizer as supplied e.g., by Applied Biosystems Inc. (Fosters, Calif., USA) or by standard molecular biology techniques.

A "serotype" is traditionally defined on the basis of a lack of cross-reactivity between antibodies to one virus as compared to another virus. Such cross-reactivity differences are usually due to differences in capsid protein sequences/antigenic determinants (e.g., due to VP1, VP2, and/or VP3 sequence differences of AAV serotypes). Under the traditional definition, a serotype means that the virus of interest has been tested against serum specific for all existing and characterized serotypes for neutralizing activity and no antibodies have been found that neutralize the virus of interest. As more naturally occurring virus isolates are discovered and capsid mutants generated, there may or may not be serological differences with any of the currently existing serotypes. Thus, in cases where the new AAV has no serological difference, this new AAV would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or variant of a given serotype. By way of example, rAAV vector include various naturally and non-naturally occurring serotypes. Such non-limiting serotypes include AAV-1, -2, -3, -4, -5, -6, -7, -8, -9, -10, -11, -rh74, -rh10, AAV-DJ and AAV-2i8. Again, for the sake of convenience, serotypes include AAV with capsid sequence modifications that have not been fully characterized as being a distinct serotype, and may in fact actually constitute a subgroup or variant of a known serotype.

The term "transgene" is used to refer to a non-native nucleic acid with respect to the AAV nucleic acid sequence. It is used to refer to a polynucleotide that can be introduced into a cell or organism. Transgenes include any polynucleotide, such as a gene that encodes a polypeptide or protein, a polynucleotide that is transcribed into an inhibitory polynucleotide, or a polynucleotide that is not transcribed (e.g., lacks an expression control element, such as a promoter that drives transcription). A transgene of the invention may comprise at least two nucleotide sequences each being different or encoding for different therapeutic molecules. The at least two different nucleotide sequences may be linked by an IRES (internal ribosome entry sites) element, providing a bicistronic transcript under control of a single promoter. Suitable IRES elements are described in e.g., Hsieh et al. (1995, Biochemical Biophys. Res. Commun. 214:910-917). Furthermore, the at least two different nucleotide sequences encoding for different (therapeutic) polypeptides or proteins may be linked by a viral 2A sequence to allow for efficient expression of both transgenes from a single promoter. Examples of 2A sequences include foot and mouth disease virus, equine rhinitis A virus, Thosea asigna virus and porcine teschovirus-1 (Kim et al., PLoS One (2011) 6(4): e18556). A transgene is preferably inserted within the rAAV genome or between ITR sequences as indicated above. A transgene may also be an expression construct comprising an expression regulatory element such as a promoter or transcription regulatory sequence operably linked to a coding sequence and a 3' termination sequence.

In a cell having a transgene, the transgene has been introduced/transferred/transduced by rAAV "transduction" of the cell. A cell or progeny thereof into which the transgene has been introduced is referred to as a "transduced" cell. Typically, a transgene is included in progeny of the transduced cell or becomes a part of the organism that develops from the cell. Accordingly, a "transduced" cell (e.g., in a mammal, such as a cell or tissue or organ cell), means a genetic change in a cell following incorporation of an exogenous molecule, for example, a polynucleotide or protein (e.g., a transgene) into the cell. Thus, a "transduced" cell is a cell into which, or a progeny thereof in which an exogenous molecule has been introduced, for example. The cell(s) can be propagated and the introduced protein expressed, or nucleic acid transcribed.

"Transduction" refers to the transfer of a transgene into a recipient host cell by a viral vector. Transduction of a target cell by an rAAV vector of the invention leads to transfer of the transgene contained in that vector into the transduced cell. "Host cell" or "target cell" refers to the cell into which the DNA delivery takes place, such as the synoviocytes or synovial cells of an individual. AAV vectors are able to transduce both dividing and non-dividing cells.

"Gene" or "coding sequence" refers to a DNA or RNA region which "encodes" a particular protein. A coding sequence is transcribed (DNA) and translated (RNA) into a polypeptide when placed under the control of an appropriate regulatory region, such as a promoter. A gene may comprise several operably linked fragments, such as a promoter, a 5' leader sequence, an intron, a coding sequence and a 3' nontranslated sequence, comprising a polyadenylation site or a signal sequence. A chimeric or recombinant gene is a gene not normally found in nature, such as a gene in which for example the promoter is not associated in nature with part or all of the transcribed DNA region. "Expression of a gene" refers to the process wherein a gene is transcribed into an RNA and/or translated into an active protein.

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. "Operably linked" means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked.

An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence is designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g., by the application of a chemical inducer. A "tissue specific" promoter is preferentially active in specific types of tissues or cells. The selection of an appropriate promoter sequence generally depends upon the host cell selected for the expression of a DNA segment. Alternatively, a transgene is to be operably linked to a promoter that allows for efficient systemic expression. Suitable promoter sequences are CMV (cytomegalovirus) promoter, CBA (chicken beta actin), or liver specific promoters such as human alpha-1 anti-trypsin (hAAT) or TBG (thyroxine binding globulin).

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have substantially different overall lengths, local alignments, such as those using the Smith Waterman algorithm, are preferred. Alternatively, percentage similarity or identity may be determined by searching against public databases, using algorithms such as FASTA, BLAST, etc.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

As used herein, "gene therapy" is the insertion of nucleic acid sequences (e.g., a transgene as defined herein) into an individual's cells and/or tissues to treat a disease. The transgene can be a functional mutant allele that replaces or supplements a defective one. Gene therapy also includes insertion of transgene that are inhibitory in nature, i.e., that inhibit, decrease or reduce expression, activity or function of an endogenous gene or protein, such as an undesirable or aberrant (e.g., pathogenic) gene or protein. Such transgenes may be exogenous. An exogenous molecule or sequence is understood to be molecule or sequence not normally occurring in the cell, tissue and/or individual to be treated. Both acquired and congenital diseases are amenable to gene therapy.

A "therapeutic polypeptide" or "therapeutic protein" is to be understood herein as a polypeptide or protein that can have a beneficial effect on an individual, preferably said individual is a human, more preferably said human suffers from a disease. Such therapeutic polypeptide may be selected from, but is not limited to, the group consisting of an enzyme, a cytokine, an antibody, a growth factor, a hormone and an anti-inflammatory protein.

A "therapeutically-effective" amount as used herein is an amount that is sufficient to alleviate (e.g., mitigate, decrease, reduce) at least one of the symptoms associated with a disease state. Alternatively stated, a "therapeutically-effective" amount is an amount that is sufficient to provide some improvement in the condition of the individual.

In this document and in its claims, the verb "to comprise" and its conjugations is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 10% of the value.

DETAILED DESCRIPTION OF THE INVENTION

Recombinant adeno-associated virus (rAAV) vector based gene therapy has proven to be successful in treating genetic disorders in clinical settings. However, upon administration of rAAV vectors, antibodies (also referred to as immunoglobulins) that are capable of neutralizing rAAV vector can have a dramatic impact on transduction. Such antibodies can be present when a subject selected for gene therapy has been infected with wild-type AAV earlier. Therefore, in a clinical setting the current practice is to test subjects for the presence of neutralizing antibodies prior to rAAV vector administration in order to avoid such neutralization. Hence, the presence of neutralizing antibodies is an exclusion criterion in current gene therapy treatments with AAV. For example, when a subject has neutralizing antibodies for AAV8, e.g. because said subject has previously been infected by wild-type AAV8, such a subject is excluded from a treatment with an rAAV8 vector. It is understood that the rAAV vector that is used may not necessarily have a wild-type capsid composed of wild-type VP proteins but may also be constituted from VP proteins that are derived from a wild-type protein and thus may not have an exact wild-type sequence. Nevertheless, nAb may be detected against capsids derived from a wild-type capsid. For many indications it is envisioned that subjects may have to undergo more than one gene therapy treatment in their life time. Because a first administration with an rAAV vector in a naïve subject generally can result in triggering neutralizing antibodies, a subsequent treatment with the same or similar rAAV vector would not be successful due to neutralizing antibodies that were induced in response to the prior treatment with rAAV which neutralizing antibodies may recognize the rAAV vector to be used in the second treatment.

To overcome this problem, it has been suggested to switch capsids, e.g. use a different serotype, for any subsequent treatment to avoid neutralizing antibodies. Avoiding neutralizing antibodies cannot be regarded to be a solution because suitable alternative serotypes are not always generally available. Such alternative serotypes or capsids are required to have the same tropism, and said subjects need to have a naïve immunity for the alternative capsid or serotype. Hence, as said, other strategies in the prior art that have been suggested to overcome pre-existing antibodies include plasma exchange and the use of immunosuppressive regimens. Such strategies have been tested in animal models with limited success, being somewhat effective in subjects having low nAb titers.

Surprisingly, the current inventors have now found that subjects with neutralizing rAAV antibody titers in the blood, which include subjects with high titer neutralizing antibodies, can have rAAV administered after such subjects are treated with an extracorporeal treatment of the blood that depletes immunoglobulins using immunoadsorption. Without being bound by theory, such depletion of immunoglobulins by immunoadsorption may also be advantageous in any subject that is to be treated with an rAAV vector, regardless of whether neutralizing antibodies have been detected prior to said immunoadsorption or not. Hence, in one embodiment an rAAV vector is provided for use in the treatment of a subject, wherein said subject has been subjected to an extracorporeal depletion of immunoglobulins using immunoadsorption prior to administration of said rAAV vector. To phrase differently, in accordance with the invention an rAAV vector for use in the treatment of a subject is provided, wherein said subject has been subjected to an extracorporeal immunoadsorption of immunoglobulins prior to administration of said rAAV vector. It is understood that with regard to suitable subjects, these comprise preferably mammals, such as a mammal selected from the group consisting of humans, non-human primates (such as for examples apes, gibbons, gorillas, chimpanzees, orangutans, macaques), domestic animals (such as for example dogs and cats), farm animals (such as for example poultry such as chickens and ducks, horses, cows, goats, sheep, pigs). More preferably, such a mammal is a primate. In a more preferred embodiment, the subject is a human.

Immunoadsorption in accordance with the invention is defined as a procedure that removes immunoglobulins from a body fluid such as the blood. Immunoadsorption involves the use of a binding moiety that is capable of binding immunoglobulins. Said immunoglobulins bound to the binding moiety allows to separate the immunoglobulins from the blood, preferably from the blood plasma or serum. Immunoadsorption hence can selectively remove immunoglobulins from the blood while retaining substantially the same composition thereof.

It is understood that with an extracorporeal depletion of immunoglobulins is meant a treatment of a body fluid that is outside of the subject's body. Such an extracorporeal depletion of immunoglobulins can involve a depletion of immunoglobulins from the blood. Such an extracorporeal depletion of immunoglobulins can also involve a depletion of immunoglobulins from cerebrospinal fluid (CSF). For example, blood may be withdrawn from the subject followed by subjecting the withdrawn blood to said depletion of immunoglobulins after which the blood is subsequently administered back to said subject. Immunoadsorption of a body fluid can be carried out separate from the body of a subject, e.g. a human. Immunoadsorption of a body fluid can also be carried out continuously. For example, the body fluid such as blood may be continuously withdrawn from a vein, the blood (e.g. whole blood or a component thereof) subsequently subjected to immunoadsorption, and re-infused back to the subject (e.g. (reconstituted blood). As shown in the examples, such methods also may include the separation of the blood into blood plasma and a fraction comprising cellular components, wherein the blood plasma is subjected to immunoadsorption, after which the obtained blood plasma that has been subjected to immunoadsorption is recombined with the cellular components and infused back to the subject (see FIG. 1A). With regard to depletion of immunoglobulins, it is understood to comprise a reduction of the concentration of the immunoglobulins.

For example, the total amount of immunoglobulins may be reduced at least twofold. Preferably, the total amount of immunoglobulins is reduced at least fourfold, eightfold, tenfold, 20-fold, 30-fold, 40-fold, 50-fold, 60-fold, 70-fold, 80-fold, 90-fold, 100-fold, 150-fold, 200-fold, 250-fold, 300-fold, 500-fold, 1000-fold, or more. The fold reduction of immunoglobulins may be detected by measuring one of the subclasses of immunoglobulins, e.g. IgA, IgD, IgE, IgG or IgM in the body fluid, e.g. blood serum or plasma, representative of the total amount of immunoglobulins. In general in serum, about 80% of immunoglobulins is IgG, 15% is IgA, 5% is IgM, 0.2% is IgD and a trace is IgE. The fold reduction of immunoglobulins may also be detected by measuring only IgG in the body fluid, e.g. blood serum or plasma, which can be regarded to be representative of the total amount of immunoglobulins. The fold reduction of immunoglobulins may also be detected by measuring at least one of IgG, IgA and IgM in the body fluid, e.g. blood serum or plasma, which is representative of the total amount of immunoglobulins. The fold reduction of immunoglobulins may also be detected by measuring all of the subclasses of immunoglobulins, e.g. IgA, IgD, IgE, IgG or IgM in the body fluid, e.g. blood serum or plasma, representative of the total amount of immunoglobulins. For example, from blood plasma or serum, the amount of IgG is measured before immunoadsorption and compared with the amount of IgG after immunoadsorption to calculate the fold reduction of IgG, which can be representative for the fold reduction achieved using immunoadsorption. Serum immunoglobulins (IgG, IgA and IgM) levels can e.g. be determined by a commercial nephelometry assay using a BN-II device (Dade Behring, Marburg, Germany). The manufacturer indicates the following reference intervals for healthy adults: IgA 70-400 mg/dl, IgG 700-1600 mg/dl and IgM 40-230 mg/dl (Dati et al., Eur J Clin Chem Clin Biochem. 1996; 34:517-20.

Alternatively, the AAV neutralizing antibody titer and/or AAV binding antibody titer may be determined before and after immunoadsorption. As shown in the example section, 3 cycles of immunoadsorption can result in an up to 16-fold reduction of AAV neutralizing antibody titer (see FIGS. 2A-2B). Without being bound by theory, 4 cycles of immunoadsorption can reduce the AAV neutralizing antibody titer about 40-fold, whereas 5 cycles of immunoadsorption can reduce AAV neutralizing antibody titer up to 100-fold. AAV neutralizing antibody titer and AAV binding antibody assays are well known in the art and the skilled person is well capable of performing such assays (such as i.a. described by Ito et al., Ann Clin Biochem 2009; 46: 508-510). Briefly, AAV neutralizing antibody titers are determined by measuring the residual expression of a (reporter) gene in cells after transduction with an rAAV vector that has been pre-incubated with a dilution series of a test-serum. The output of such an assay can be expressed as the first dilution at which 50% or greater inhibition of the reporter signal is detected (e.g. amount of cells transduced and/or amount of expressed transgene). AAV binding antibody titer can be determined with an ELISA. Briefly, microtiter plates can be coated with intact particles of recombinant AAV vectors which are incubated with dilution series of test-serum, followed by incubation with a horseradish peroxidase-conjugated anti-human immunoglobulin G (HRP-IgG). It is understood that it is not required to determine the fold reduction of immunoglobulins, neutralizing antibody titer or AAV binding antibody titer in a subject that is to have rAAV administered. Nevertheless, one may monitor the fold reduction in a subject and once the desired reduction in e.g. immunoglobulins is achieved the rAAV vector can be administered.

It is understood that the number of cycles of immunoadsorption correlates to fold reduction in immunoglobulins, either measured by determining the fold reduction of a particular immunoglobulin subclass or specific immunoglobulin titer such as AAV binding/neutralizing antibodies. Hence, the skilled person is well capable of determining the conditions such as the number of cycles required to achieve a certain reduction of immunoglobulins in any subject. With regard to the number of cycles of immunoadsorption, it is understood that with regard to the processing of blood plasma 1 cycle corresponds to the processing of a 1 volume of blood plasma as calculated according to Sprenger et al. (Sprenger, et al. J Clin Apher. 1987; 3: 185-190), which is incorporated by reference herein in its entirety. Hence, in another aspect of the invention, immunoadsorption comprises at least 2, at least 3, at least 4, at least 5, at least 6, at least 7, at least 8, at least 9 or at least 10 cycles of immunoadsorption.

With regard to depletion of immunoglobulins using immunoadsorption it is understood that such a method is not a method of plasma exchange. As said, plasma exchange methods are widely known in the art and have been suggested and used in rAAV vector administrations. Plasma exchange involves the continuous withdrawal of blood from a vein, which blood is anticoagulated, after which it is separated into its liquid, i.e. plasma, and cellular components by e.g. hemofiltration. The separated plasma in plasma exchange is replaced either by plasma from a donor (e.g. not having neutralizing antibodies) or by a defined replacement fluid such as e.g. a saline solution with 5% albumin. That immunoadsorption is not plasma exchange does not exclude to use depletion of immunoglobulins by using immunoadsorption in combination with plasma exchange. Hence, as long as the subject has been subjected to depletion of immunoglobulins by immunoadsorption, the use of an rAAV vector in accordance with the invention is contemplated.

Furthermore, the application of immunoadsorption according to the invention does not exclude to use depletion of immunoglobulins by using immunoadsorption in combination with other interventions. For example, subjects may also be subjected to immune suppression regimens well known in the art that are aimed at reducing immune responses, which can include reducing the humoral response, induced by treatment with rAAV. Subjects may also be subjected to strategies to induce immune tolerance to AAV capsids. Hence, the subjects that are to have rAAV administered and are to be subjected to the extracorporeal treatment may be subjected to other concomitant interventions that are also aimed at reducing the humoral immunity and/or cellular immunity. Such interventions may for example be used in a first treatment with rAAV, wherein in any subsequent treatment immunoadsorption in accordance with the invention may be applied. In subsequent treatments such interventions may be applied as well. As said, immunoadsorption in accordance with the invention is defined as the use of a binding moiety that is capable of binding immunoglobulins such that the immunoglobulins bound to the binding moiety can be separated from the blood, preferably from the blood plasma. Such a binding moiety may be any kind of binding moiety, as long as it is capable of selectively binding to immunoglobulins. Such binding moieties preferably bind at least one of IgA, IgD, IgE, IgG and IgM. Such binding moieties may bind IgA, IgD, IgE, IgG or IgM. In one embodiment the binding moieties may bind predominant immunoglobulins that are present in the blood, such as IgG, IgA and IgM, most preferably IgG. It is understood that a binding moiety or binding moieties for one or more immunoglobulins may be selective, e.g. IgG may be bound by a binding moiety whereas the other immunoglobulins are not substantially bound or IgG, IgA and IgM are bound whereas the other immunoglobulins are not substantially bound. Preferably however such binding moieties bind the immunoglobulins IgA, IgD, IgE, IgG and IgM. It is also understood that the binding moieties in accordance with the invention may be selected that also bind immunocomplexes, i.e. immunoglobulins bound to antigens. Such binding moieties may include one or more binding moieties selected from the group consisting of peptides (such as e.g. Gam-146 and phenyl-alanine), dextran sulfate, tryptophan, protein A, protein G, protein A/G, protein L, and anti-human immunoglobulin antibodies. In one embodiment the binding moiety is a protein or a peptide or an aptamer.

The binding moieties according to the invention are preferably attached to a matrix. Such attachment or coupling to a matrix may be covalent or non-covalent. Suitable matrices are e.g. cellulose, sepharose, silica, cellulose, and polyvinyl-ethanol. Many suitable matrices are known in the art as well as suitable methods to covalently or non-covalently attaching the binding moieties thereto. The binding moieties attached to a matrix allows contacting e.g. of blood plasma therewith to allow binding of immunoglobulins thereto and separate immunoglobulins bound to said binding moiety from the blood plasma. Hence, a suitable binding moiety non-covalently or covalently attached to the matrix in accordance with the invention is selected such that the binding moiety remains attached to the matrix during interaction with blood plasma and/or serum or the like.

The binding of the immunoglobulin may be carried out by using a column or a device. The term device or column can be used interchangeably and is understood to mean any suitable carrier to comprise a binding moiety or a matrix with binding moiety in which the binding of the immunoglobulin, i.e. immunoadsorption, is to take place. Hence, said column or device preferably comprises a matrix with binding moiety. The amount of matrix with binding moiety that is used provides for a sufficient binding capacity to bind immunoglobulin. It is understood that sufficient binding capacity is easily attained by e.g. using a two-column setup as shown in the examples with the commercially available system LIFE 18 Apheresis Unit (item nr. 330-000-098, Miltenyi Biotec GmbH, Bergisch Gladbach, Germany), wherein one column is being regenerated while the other is processing plasma (see FIG. 1A). Such a column can comprise filters at either end to prevent particulate matter from entering or leaving the column. Hence, when the blood of a subject is separated into plasma and cellular components, the plasma fraction flows through the column. The plasma and/or blood also be processed into serum by removing clotting proteins. Anti-clotting agents may also be added. Removal of clotting proteins from plasma and/or adding anti-clotting agents (e.g. heparin) may improve flow through the column and/or interaction with the binding moieties. The plasma or serum is thus passed through such a column in accordance with the invention and the plasma or serum collected while immunoglobulin bound to the binding moiety is retained in the column. After the plasma or serum from which immunoglobulins are depleted is collected, the blood can be reconstituted and returned to the subject.

Commercially available devices, or columns, that are suitable for the invention include Immunosorba® (Fa. Fresenius HemoCare, St. Wendel) which uses as a binding moiety staphylococcal protein A and has Sepharose as a matrix; Prosorba® (Fa. Fresenius HemoCare, St. Wendel) which has as a binding moiety staphylococcal protein A and silica as a matrix; Globaffin® (Fa. Fresenius HemoCare, St. Wendel) which uses an immobilized synthetic peptide GAM® as a binding moiety with a Sepharose CL-4B matrix, which binding properties similar to those of the protein A; Therasorb® Ig flex (Miltenyi Biotex, Bergisch Gladbach, Germany) which uses polyclonal sheep anti-human Ig with Sepharose CL-4B as a matrix; Selesorb® (Kaneka Medical Products, Osaka Japan), which uses a dextran sulfate binding moiety and a cellulose gel as a matrix; Immusorba® (Fa. ASAHI/Diamed, Cologne) are based on tryptophan (TR-350L) or phenylalanine binding moiety (PH-350L), which are attached to a polyvinylethanol-gel matrix. Such commercially available columns, or the like, can be well used in accordance with the invention, for example in a two-column device like the LIFE 18 Apheresis Unit (Miltenyi) or the Art Universal (Fresenius Medical Care).

In one embodiment, the binding moiety in accordance with the invention is a binding moiety that is capable of binding anti-AAV immunoglobulins. It is understood that such a binding moiety may be specific for anti-AAV immunoglobulins. Hence, in a further embodiment such a binding moiety is capable of binding specifically anti-rAAV immunoglobulins. With regard to specificity of binding moieties it is understood that the majority of immunoglobulins will not be specific for AAV, hence, by selectively binding anti-AAV immunoglobulins the circulating antibody repertoire is to remain largely intact with the exception of anti-AAV immunoglobulins which are to be depleted. Selectivity of a binding moiety can easily be determined with immunoglobulin assays such as described above. For example, the total amount of immunoglobulins (or a subgroup thereof) may not be significantly affected by immunoadsorption whereas the AAV binding/neutralizing antibodies are reduced. It is understood that in this embodiment such a binding moiety preferably is a protein, as AAV capsids comprise protein. For example, AAV epitopes which are known to be capable of generating anti-AAV antibodies can be used as binding moieties. Such epitopes can be attached to a suitable matrix and be presented such to mimic binding sites as present in an AAV capsid. Also, AAV capsid proteins, such as VP1, VP2 and/or VP3, may be used as binding moieties. AAV capsids may also be used as binding moieties for binding anti-rAAV immunoglobulins. Preferably, the peptides, AAV proteins or AAV capsids used as binding moieties for binding immunoglobulins are derived from the AAV serotypes which is to be administered. It is understood that AAV capsids comprise empty capsids and/or full capsids. It is also understood that AAV capsids used as binding moieties may also be the actual product that is to be administered to the subject. The binding moieties capable of binding anti-rAAV immunoglobulins, as for any other binding moiety as described above, may be attached to any appropriate matrix. As said, such attachment may be covalent or non-covalent. A suitable non-covalent attachment may include the binding of a suitable AAV capsid via an AAV specific antibody (such as a nanobody). For example, a chromatography resin commercially available for binding AAV of at least serotypes 1, 2, 3 and 5 is AVB Sepharose High Performance (GE Healthcare Bio-Sciences, Pittsburgh, USA, i.a. product code 28411202). Hence, AAV capsids bound to this resin may be used as a suitable binding moiety/matrix in accordance with the invention. Also, e.g. for AAV5 capsids, a sialic-acid-rich protein called mucin covalently attached to a sepharose was shown suitable to bind AAV capsids non-covalently (Mol Ther. 2001 October; 4(4):372-4). Although such capsids are not covalently bound to said matrices, such capsids may not easily be released from the matrix. This is because high salt concentrations and/or extreme pH values are required to release the capsids, which extreme concentrations and pH values are not compatible with blood plasma and/or serum. Hence, a binding moiety non-covalently attached to a matrix is selected such that the binding moiety remains attached during interaction with blood plasma and/or serum or the like. In addition, as the subject is to be administered with a corresponding AAV product any minor leakage from such a non-covalently attached AAV capsid in addition to the later on administered AAV product does not provide any risk from a safety point of view as said capsid is also comprised in the administered AAV product. Capsids may also be covalently attached to cyanogen-bromide-activated Sepharose 4B (GE Healthcare Bio-Sciences, Pittsburgh, USA, i.a. product code 17-0430-01) via —$NH_2$ groups.

In any case, such AAV specific binding moieties attached to a matrix may be used in accordance with the invention as described above. Such immunoadsorption advantageously resulting in reducing AAV binding/neutralizing antibodies while retaining most of the other immunoglobulins. In addition, these may also be used in a combined fashion. For example, the body fluid may first be subjected to immunoadsorption that is selective for immunoglobulins, followed by a second immunoadsorption that is selective for immunoglobulins that can bind AAV capsids which may be in series or in parallel (see FIGS. 1B and 1C). The body fluid may also be first subjected to immunoadsorption that is selective for immunoglobulins that can bind AAV capsids followed by a second immunoadsorption that is selective for immunoglobulins, or one can even envisage both types of immunoadsorption to be carried simultaneously. In any case, it is preferred to have the body fluid first subjected to immunoadsorption that is selective for immunoglobulins, followed by a second immunoadsorption that is selective for immunoglobulins that can bind AAV capsids. The first immunoadsorption reduces the total amount of immunoglobulins in the body fluid, e.g. blood serum or plasma, whereas the second immunoadsorption reduces AAV specific immunoglobulins that remain. Hence, advantageously, the total AAV binding/neutralizing antibody titer can be reduced even further. Hence, in another embodiment, an rAAV vector is provided for use in the treatment of a subject according to the invention, wherein said immunoadsorption comprises two immunoadsorptions, one immunoadsorption with a binding moiety that binds immunoglobulins and one immunoadsorption that comprises a binding moiety that binds anti-rAAV immunoglobulins. Said two immunoadsorptions may comprise one immunoadsorption with a binding moiety that binds selectively immunoglobulins and one immunoadsorption that comprises a binding moiety that selectively binds anti-rAAV immunoglobulins.

With regard to the treatment of a subject, said subject may be a subject having (or being suspected to have) AAV binding/neutralizing antibodies prior to said extracorporeal depletion of immunoglobulins using immunoadsorption. This may be because the subject has been treated with an rAAV vector before, or because the subject has been exposed to wild-type AAV. The presence of AAV binding and/or neutralizing antibodies may be determined using an assay such as described in the example section. AAV binding antibody titers can be measured using ELISA. Briefly, AAV capsid proteins are immobilized on polystyrene ELISA plates and incubated with dilution series of serum samples to be tested. Bound antibodies can subsequently be detected by incubation with conjugated antibodies against immunoglobulins bound to AAV capsid proteins. rAAV neutralizing antibody titer can be determined by using a cell-based assay, in which rAAV is pre-incubated with a dilution series of a serum sample after which cells are infected with said pre-incubated rAAV and transduction efficiency and/or transgene expression is determined. The output of such an assay typically is the dilution at which less than 50% of transduction efficiency and/or transgene expression is detected, as compared with a control (e.g. un-incubated rAAV or rAAV pre-incubated with control serum). As can be observed in the example section, the detection of neutralizing antibodies can vary with regard to its sensitivity which may differ when e.g. different cells are used between assays (see FIGS. 2A and 2B and take note at the scale of the y-axis). Nevertheless, the trends observed between assays can be similar. It is understood that it may not be necessary to carry out any assays on body fluids obtained from a subject for detection of such binding/neutralizing antibodies, as it can also be envisaged that in any case, the depletion or reduction of rAAV binding/neutralizing antibodies in accordance with the invention generally obtained can be sufficient to allow administration of rAAV to any subject in a population. Nevertheless, it may be preferred to carry out an assay for determining the rAAV binding/neutralizing antibody titer prior to rAAV administration. Hence, in another embodiment, the rAAV vector for a use in the treatment of a subject according invention, comprises the treatment of a subject having neutralizing antibodies for the capsid of said rAAV vector prior to said extracorporeal treatment. Also, in another embodiment, the rAAV vector for a use in the treatment of a subject according invention, comprises the treatment of a subject having binding antibodies for the capsid of said rAAV vector prior to said extracorporeal treatment.

In one embodiment, the rAAV vector for use in the treatment of a subject according invention, wherein said treatment comprises a subject having neutralizing antibodies for the capsid of said rAAV vector prior to said extracorporeal depletion of immunoglobulins as described above. In another embodiment, the rAAV vector for use in the treatment of a subject according to invention, comprises the treatment of a subject having received a previous treatment with an rAAV vector. Hence, in one embodiment an rAAV vector is provided for use in the treatment of a subject, wherein said subject has been subjected to an extracorporeal depletion of immunoglobulins using immunoadsorption prior to administration of said rAAV vector, and wherein said subject has received a previous treatment with an rAAV vector. Preferably, the rAAV serotypes used in the previous treatment and subsequent treatment are the same. Preferably, the rAAV capsids used in the previous treatment and subsequent treatment are the same. In another embodiment, the capsid proteins of the rAAV vector of the first administration and the capsid proteins of the rAAV vector of the second administration are different from each other. Preferably, the previous and subsequent treatment, i.e. the first and second treatment, are at least 1 year apart. It is also understood that the subsequent rAAV vector administrations may also comprise more than two administrations. The subsequent rAAV vector administrations may comprise at least two subsequent administrations, at least three subsequent administrations and so forth.

Advantageously, it was found that by applying immunoadsorption to deplete immunoglobulins from a subject, the delivery of rAAV to the target cell, i.e. transduction of the target cell, a similar or the same dose could be used in a subject as compared with the dose used in a subject being naïve (i.e. unexposed) to the corresponding AAV capsid serotype. In another embodiment, the rAAV vector for use in the treatment of a subject in accordance with the invention comprises the same dose of rAAV vector as compared with the dose administered to a subject not having neutralizing antibodies for said capsid. In a further embodiment, the rAAV vector for use in the treatment of a subject in accordance with the invention comprises a dose of rAAV vector which is at most 2-fold higher as compared with the dose for a subject not having neutralizing antibodies for said capsid.

Without being bound by theory, it is understood that the extracorporeal depletion of immunoglobulins may also be advantageous in subjects that do not necessarily have any detectable neutralizing antibodies. As can be observed in the example section, the detection of neutralizing antibodies involves a biological assay which can vary with regard to its sensitivity. Nevertheless, regardless of any neutralizing antibodies detected, antibodies present in the blood, or another bodily fluid, may still interact with rAAV thereby hampering delivery to the target cells. Hence, in another embodiment, the extracorporeal depletion of immunoglobulins may advantageous improve the potency of the rAAV vector being administered. Potency being defined as the number of cells being transduced and/or the amount of transgene expressed in the cell. Hence, without being bound by theory, the number of cells being transduced and/or the amount of transgene being expressed in the cell may be improved in a subject that has been subjected to extracorporeal depletion of immunoglobulins prior to administering the rAAV vector. In another embodiment, the rAAV vector for use in the treatment of a subject in accordance with the invention comprises a dose of rAAV vector which is lower as compared with the dose for a subject not having any detectable neutralizing antibodies for said capsid. In a further embodiment, said dose is at least 20%, at least 30%, at least 40% or at least 50% or more lower as compared with the dose required to achieve a defined transduction level in a subject not being subject to the extracorporeal depletion of immunoglobulins. A desired transduction can be defined e.g. as resulting a certain expression level in the subject by measuring the amount of transgenic protein detected in e.g. the blood, or any other appropriate measurement known in the art to determine transduction in a subject.

In one embodiment, the rAAV vector for use in the treatment of a subject according to the invention wherein the administration is selected from the group consisting of an intravenous administration, an intramuscular administration, intra-hepato arterial administration, portal vein administration, intraperitoneal administration, intracoronal administration. Routes of administration that are in particular useful are routes wherein neutralizing antibodies may be encountered upon administration. Such routes may include an administration route wherein the rAAV vector is exposed to blood and/or cerebrospinal fluid. It is understood that such a route of administration may also comprise administration to the central nervous system. Neutralizing antibodies may for example hamper intrathecal administration of rAAV or stereotactic injections in the brain and/or spinal cord when e.g. the blood brain barrier function is compromised.

In another embodiment, the rAAV vector for a use in the treatment of a subject in accordance with the invention, comprises an extracorporeal immunoadsorption that is at most 24 hours prior to administration of said rAAV vector. Preferably the time period between said rAAV vector administration and said extracorporeal immunoadsorption (also referred to as extracorporeal depletion of immunoglobulins using immunoadsorption) is short. Preferably, the said rAAV vector administration and extracorporeal immunoadsorption are at most 24, 23, 22, 21, 20, 19, 18, 17, 16, 15, 14, 13, 12, 11, 10, 9, 8, 7, 6, 5, 4, 3, 2 or 1 hours apart. Preferably said rAAV vector administration and extracorporeal immunoadsorption are performed sequentially at most 50, 40 or 30 minutes apart. Most preferably said rAAV vector administration and extracorporeal immunoadsorption are performed sequentially without any substantial pause, i.e. immediately following the extracorporeal immunoadsorption procedure said rAAV vector is to be administered.

Accordingly, in accordance with the current invention as described above, a method is provided for reducing the anti-rAAV immunoglobulin concentration in a body fluid, comprising the steps of:
a) providing a body fluid;
b) providing a device for immunoadsorption;
c) subjecting the body fluid to immunoadsorption for anti-rAAV using said device.

It is understood that a body fluid in accordance with the invention may be any kind of body fluid, i.e. blood plasma, or blood serum, or cerebrospinal fluid. Hence, in accordance with the current invention as described above, a method is also provided for reducing the anti-rAAV immunoglobulin concentration in the blood, comprising the steps of:
a) providing blood;
b) providing a device for immunoadsorption;
c) separating the blood provided in a) in plasma components and cellular components;
d) subjecting the plasma components obtained in c) to immunoadsorption by using the device provided in b);
e) reconstituting the blood by combining the cellular components obtained in c) with the plasma components subjected to immunoadsorption obtained in d).

In accordance with the invention also a method is provided for reducing the anti-rAAV immunoglobulin concentration in the blood of a subject, comprising the steps:
a) providing blood of the subject;
b) providing a device for immunoadsorption;
c) separating the blood provided in a) in plasma components and cellular components;
d) subjecting the plasma components obtained in step c) to immunoadsorption by using the device provided in step b);
e) reconstituting the blood by combining the cellular components obtained in c) with the plasma components subjected to immunoadsorption obtained in d);
f) administering the reconstituted blood obtained in step e) to the subject. Such method may comprise in addition the step g) comprising administering to the subject an rAAV vector.

The transgene contained within the viral vector may not be a limitation of this invention. The invention is anticipated to be useful with any transgene. Suitable transgenes for delivery to a patient in a viral vector for gene therapy may be selected by those of skill in the art. These therapeutic nucleic acid sequences typically encode products (e.g. proteins or RNA) for administration and expression in a patient in vivo or ex vivo to treat an inherited or non-inherited genetic defect, e.g. by replacing or correcting deficiency, to treat an epigenetic disorder or disease, or to treat a condition associated with dysregulation of a gene product. Such therapeutic genes which are desirable for the performance of gene therapy include, without limitation, a very low density lipoprotein receptor gene (VLDL-R) for the treatment of familial hypercholesterolemia or familial combined hyperlipidemia, the cystic fibrosis transmembrane regulator gene (CFTR) for treatment of cystic fibrosis, DMD Becker allele for treatment of Duchenne muscular dystrophy, and a number of other genes which may be readily selected by one of skill in the art to treat a particular disorder or disease. In a preferred embodiment, the rAAV vector comprises a transgene which encodes a therapeutic protein, or an RNA, such as an miRNA. Preferably, the therapeutic protein is selected from the group consisting of factor IX (preferably human factor IX), factor VIII (preferably human factor VIII), lipoprotein lipase (LPL; including mutants such as for example $LPL^{S447X}$; see WO 01/00220 A2), porphobilinogen deaminase (PBGD), very low density lipoprotein receptor (VLDL- R), cystic fibrosis transmembrane conductance regulator (CFTR), Duchenne muscular dystrophy (DMD) Becker allele, hypoxyluria (AGXT), N-acetyl-alpha-D-glucosaminidase (NaGlu), glial cell line-derived neurotrophic factor (GDNF), S100A1 (also known as S100 calcium-binding protein A1, which in humans is encoded by the S100A1 gene). In a preferred embodiment, the therapeutic protein is factor IX, more preferably human factor IX.

Alternatively, or in combination with any one of the preceding embodiments, in a preferred embodiment, the gene therapy is for treating, preventing, curing and/or reverting a condition or disease, preferably a so-called orphan disease, which is herein understood to be a rare disease that affects a small percentage of the population, e.g. fewer than 1 in 1,500 people of the population that is life-threatening, chronically debilitating and/or inadequately treated. Generally, an orphan disease is a genetic disease and hence a life-long disease even if symptoms do not immediately appear. In a preferred embodiment such condition or disease is selected from the group consisting of lipoprotein lipase deficiency (LPLD), hemophilia B, acute intermittent porphyria (AIP), Sanfilippo B syndrome, Parkinson's Disease (PD), congestive heart failure (CHF), Hemophilia A, Huntington's disease, Duchenne Muscular Dystrophy (DMD), Leber's congenital amaurosis, X-linked severe combined immunodeficiency (SCID), adenosine deaminase deficiency severe combined immunodeficiency (ADA-SCID), adrenoleukodystrophy, chronic lymphocytic leukemia, acute lymphocytic leukemia, multiple myeloma, cystic fibrosis, sickle cell disease, hyperlipoproteinemia type I, thalassemia, Alzheimer's disease, amyotrophic lateral sclerosis (ALS), epilepsy, Friedreich's ataxia, Fanconi anemia, Batten disease, wet AMD, alfa-antitrypsin-1, Pompe disease, SMA-1, Drug-resistant non-small cell lung cancer, GM1 gangliosidosis, retina pigmentosa, homozygous Familial Hypercholesterolemia, lysosomal storage diseases, a copper or iron accumulation disorders (e.g., Wilson's or Menkes disease), lysosomal acid lipase deficiency, hypoxyluria, Gaucher's disease, Hurler's disease, adenosine deaminase deficiency, glycogen storage disease and a retinal degenerative disease (such as RPE65 deficiency, choroideremia).

Alternatively, or in combination with any one of the preceding embodiments, in a preferred embodiment, the rAAV vector composition further comprises a pharmaceutically acceptable carrier, diluents, solubilizer, filler, preservative and/or excipient. The rAAV vector bearing a therapeutic gene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose. The viral vector is administered in sufficient amounts to transfect the desired cells and provide sufficient levels of transduction and expression of the selected transgene to provide a therapeutic benefit without undue adverse or with medically acceptable physiological effects which can be determined by those skilled in the medical arts. Conventional and pharmaceutically acceptable routes of administration include direct delivery to the target organ, tissue or site, intranasal, intravenous, intramuscular, subcutaneous, intradermal, oral and other parental routes of administration. Routes of administration may be combined, if desired. Dosages of the rAAV vector will depend primarily on factors such as the condition being treated, the selected gene, the age, weight and health of the patient, and may thus vary among patients. For example, a therapeutically effective human dosage of the rAAV for primo administration is generally in the range of from about 20 to about 50 ml of saline solution containing concentrations of from about $1\times10^7$ to $1\times10^{10}$ pfu/ml viruses. A preferred adult human dosage is about 20 ml saline solution at the above concentrations. The dosage will be adjusted to balance the therapeutic benefit against any side effects. The levels of expression of the selected gene can be monitored to determine the selection, adjustment or frequency of dosage administration.

In a further aspect, the present invention relates to use of an rAAV vector for the manufacture of a medicament for the treatment of a disease, condition or disorder as specified above.

In a further aspect, the present invention relates to a kit of parts comprising an rAAV vector as defined herein, a device for immunoadsorption as defined herein. In a preferred embodiment, the kit further comprises instructions for use of the kit.

Each embodiment as identified herein may be combined together unless otherwise indicated.

BRIEF DESCRIPTION OF THE FIGURES

FIGS. 2A and 2B shows results from different neutralizing antibody titration assays using PLC/PRF/5 cells or HEK293 cells, respectively.

EXAMPLES

AAV Vectors

Figure 1A:
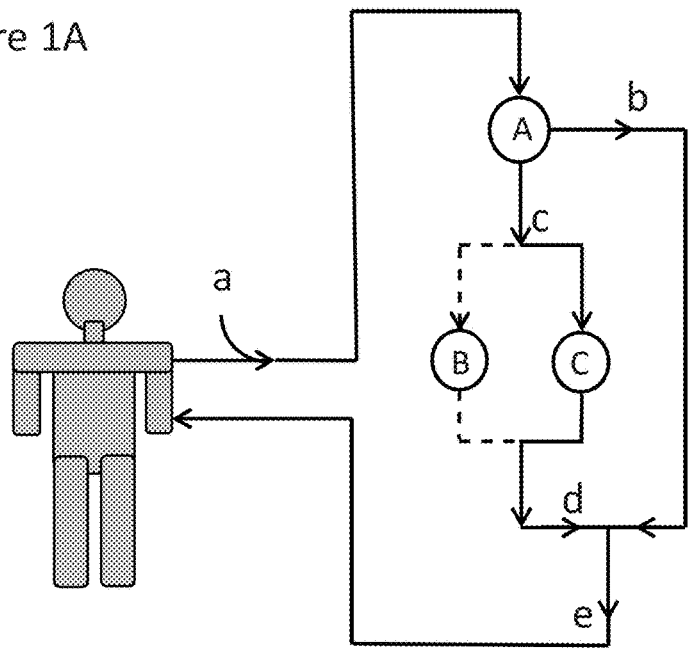
FIG. 1A: Immunoadsorption set up. From a (human) subject blood is continuously withdrawn. Optionally, an anticoagulant (heparin) may be added to the withdrawn blood. The blood is subsequently processed by a separating device (A) separating the blood into plasma (c) and cellular constituents (b). The plasma subsequently flows through an immunoadsorption column (C). The immunoadsorption set up can comprise two adsorption columns (B and C) that may be used in an alternating fashion such as in the examples. For example, while one is used for plasma processing, the other column may be cleaned. This way, the binding capacity of the columns may be used optimally. Alternatively, the columns B and C may be different types of columns that are used in an alternating fashion. The processed plasma (d) is subsequently recombined with the cellular constituents (b) and infused back (e) to the (human) subject.
Figure 1B:
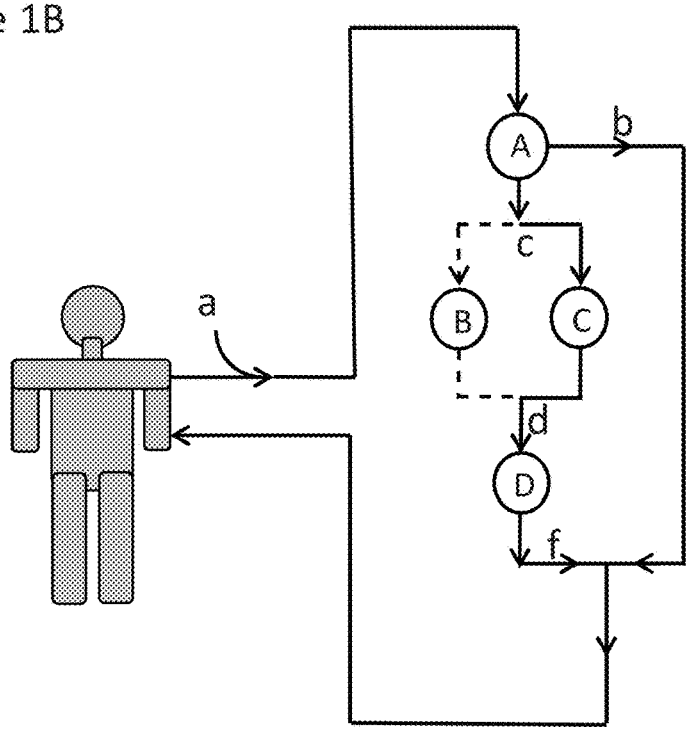
FIG. 1B: Immunoadsorption set up. From a (human) subject blood is continuously withdrawn. Optionally, an anticoagulant (heparin) may be added to the withdrawn blood. The blood is subsequently processed by a separating device (A) separating the blood into plasma (c) and cellular constituents (b). The plasma subsequently flows through an immunoadsorption column (C). The immunoadsorption set up can comprise two adsorption columns (B and C) used in an alternating fashion wherein when one is used for plasma processing, the other column is being cleaned. The processed plasma (d) is subsequently passed through a second column (D) which is different from columns B and C, e.g. an immunoadsorption specific/selective for anti-AAV immunoglobulins. The processed plasma (f) is than recombined with the cellular constituents (b) and infused back (e) to the (human) subject.
Figure 1C:
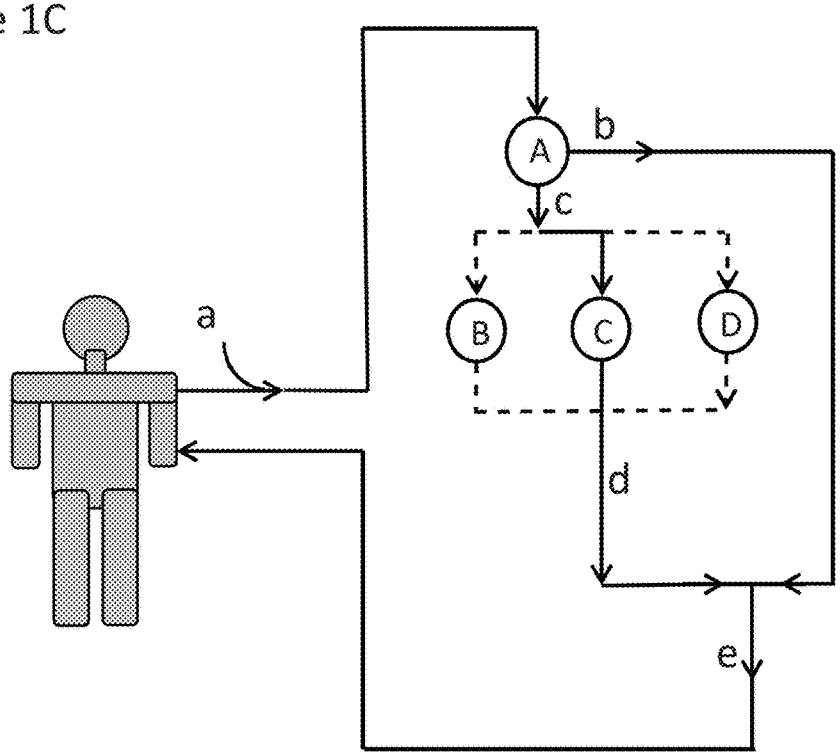
FIG. 1C: Immunoadsorption set up. From a (human) subject blood is continuously withdrawn. Optionally, an anticoagulant (heparin) may be added to the withdrawn blood. The blood is subsequently processed by a separating device (A) separating the blood into plasma (c) and cellular constituents (b). The plasma subsequently flows through an immunoadsorption column (C). The immunoadsorption set up can comprise several adsorption columns (B, C and D) used in an alternating fashion wherein when one is used for plasma processing, the other columns may be cleaned. The columns used may be different or the same. For example, columns B and C may be used in an alternating fashion as shown in the examples. Plasma processing may be switched to column D after or before one or more cycles of processing by the B/C columns. The processed plasma (d) is subsequently recombined with the cellular constituents (b) and infused back (e) to the (human) subject.

Two different AAV vectors of the serotype 5 were used (AAV5). A first vector encoded the secreted embryonic alkaline phosphates (SEAP) (AAV5-SEAP) and the second vector encoded human coagulation factor IX (hFIX) (AAV5-hFIX). Non-human primates (*Macaca fascicularis*, NHP, 3 animals per group) tested negative for the presence of anti-AAV serotype 5 neutralizing antibodies were used. The first administration of AAV5-SEAP ($1\times10^{13}$ gc/kg) was at day 0. The second administration of AAV5-hFIX ($1\times10^{13}$ gc/kg) was at day 49. At most 24 hours before the second administration immunoadsorption was performed.

Immunoadsorption

The immunoadsorption process was as follows. Blood was previously collected from the NHP in lithium-heparin tubes and stored at 4° C. for processing. After centrifugation at 3500 rpm for 5 min plasma was discarded and 1 mL of SAG-mannitol per 4 mL of whole blood was added. The blood concentrate was used to reconstitute blood to fill the LIFE 18 equipment volume for the immunoadsorption process (i.e. tubing, separator devices, immunoadsorption devices). The extracorporeal volume was about 80 ml and the blood volume of the animals was estimated to be about 8% of the bodyweight, i.e. for an animal of about 3 kg this was assessed to be about 300 ml. Animals had received heparin prior to the immunoadsorption process. Animals were cannulated at a vein and an artery and connected to the LIFE 18 equipment. Cellular components were separated from blood plasma using a filtration device LIFE 18 Disk Separator (item nr. 330-000-038, Miltenyi Biotec GmbH, Bergisch Gladbach, Germany). The plasma was subsequently passed through a Therasorb Ig flex column/device from Miltenyi (item nr. 330-000-462 Miltenyi Biotex, Bergisch Gladbach, Germany) which uses polyclonal sheep anti-human Ig with Sepharose CL-4B as a matrix. The plasma that was subjected to immunoadsorption was recombined with the cellular components. Heparin, CaCl2 and plasmalyte was added and reconstituted blood infused back to the animal.

Transgene Expression

The analysis of SEAP expression was performed with the SEAP Reporter Gene Assay, chemiluminescent (Ref: 11 779 842 001) from Sigma. This assay allows the quantitation of SEAP in the serum samples. In each plate, a negative (water) and a positive control (different concentrations serving as standard) was included. The SEAP concentration was calculated extrapolating from the SEAP standard curve. hFIX expression was measured using ELISA plates (Nunc MaxiSorp plate. Ref: 456537, Thermo Scientific) coated with 50 µL of anti-hFIX (AHIX-5041, HTI) diluted 1:3000 in carbonate buffer overnight at 4° C. The next day plates were washed three times with PBS Tween20 (PBSt) and blocked with blocking solution (PBSt+6% BSA) for one hour at RT. Plates were washed three times with 200 µL PBSt; All sera samples and all FIX standards were diluted 1:100 in incubation buffer (2% BSA in PBSt). The dilutions were added at a final volume of 100 µL and incubated for one hour at RT. All samples were tested in duplicate. All samples were tested in duplicate. Plates were washed three times with PBSt, 100 µL of HRPO-conjugated anti-hFIX were added (Ref: CL20040APHP, Cedarlane Laboratories, diluted 1:2000) and plates incubated for one hour at RT. They were then washed three times with PBSt and the reaction was revealed with TMB substrate. It was stopped after 30 min by addition of $H_2SO_4$ 2N. The absorbance was read at 450 nm in a microplate reader. The total antibody titre was calculated as the serum dilution with an absorbance five-fold higher than the negative control.

Neutralizing Antibody (NAbs) Titer

The measurement of NAbs in serum was based on an in vitro assay using AAV5 carrying the transgene luciferase (AAV5-luc) and the hepatic cell line PLC/PRF/5 (ATCC CRL-8024) or HEK293 cells. Transgene expression is revealed by addition of luciferin. Cells were seeded into a 96-well plate at a density of $10^4$ cells/well. NHP sera were prepared in DMEM/2% FBS in a total volume of 100 µL, beginning with a 1:4 dilution followed by a dilution series of 1:2. Cells were infected with $10^6$ AAV5 particles and wild type (wt) adenovirus was added at an MOI of 1. AAV was diluted in 100 µL DMEM/2% FBS and incubated with serial serum dilutions for 2 h at 37°. The mixture was then used to infect cells. Each serum dilution was tested in duplicate. Negative controls of non-infected cells as well as positive controls of infected cells without NHP serum were included in each plate. The infected cells were incubated for 48 h and luciferase activity was quantified. Light emission from each well was measured in photons/cm2/seg.

Anti-AAV Antibody Titer

The quantification of total Abs against AAV5 was based on an ELISA assay using the specific capsid to coat the plate. The presence of total Abs specific against each capsid is revealed using Protein A Peroxidase. ELISA plates (Nunc MaxiSorp plate. Ref: 456537, Thermo Scientific) were coated with antigen (AAV5 cap) at 100 ng/well in carbonate buffer overnight to 4° C. The next day plates were washed three times with PBS tween-20 (PBSt) to eliminate the rest of the antigen and blocked with blocking solution (PBS+3% FBS) to prevent unspecific binding. After washing three times with 200 µL PBSt, serum dilutions in PBSt were added, starting with 1:9 followed by a dilution series of 1:3 in a final volume of 100 µL. All samples were tested in duplicate. Negative controls without serum were included in each plate. The serum dilutions were incubated for 2 h at 37°. After this, the serum was removed, the plate was washed three times with PBSt, and 100 µL of protein A peroxidase diluted 1:10,000 in blocking solution were added for one hour. The plate was washed three times with PBSt and the reaction was revealed with TMB substrate and stopped 30 min later with $H_2SO_4$ 2N. The absorbance was read at 450 nm in a microplate reader. The total antibody titre was calculated as the serum dilution which had an absorbance five-fold higher than the negative control. The total antibody titer reduction observed was about 9-fold, which was in line with the reduction observed in the Nab assay.

Ig, IgM, IgG1 Measurements

In order to facilitate the completion of an AAV re-administration procedure in the clinical setting, the total Immunoglobulin, IgM and IgG1 concentrations were measured before and after the immunoadsorption procedure. Measurements were carried out using assays developed for *Macaca fascicularis*. Reductions in general immunoglobulins concentrations observed were compatible with the Tab assay.

Results and Discussion

Figure 2A:
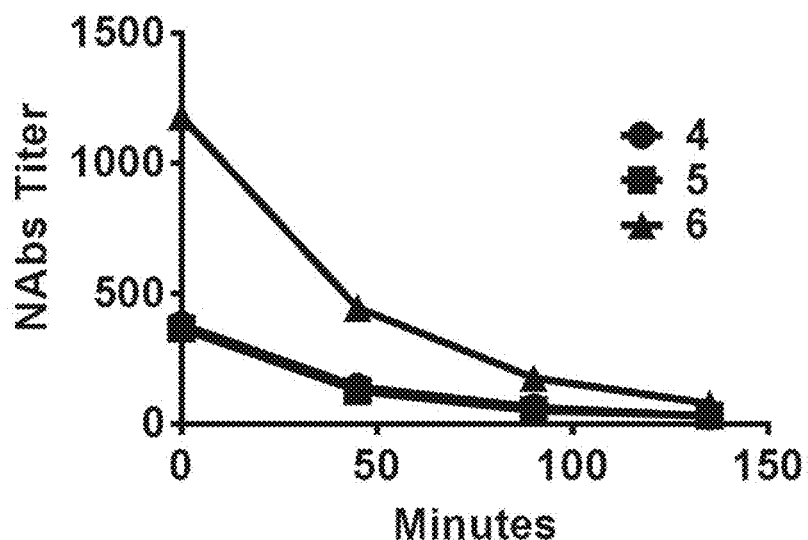
FIGS. 2A and 2B. Neutralizing antibody titer reduction during immunoadsorption. The neutralizing antibody titer was determined in plasma obtained from non-human primates (0108, 7028, 7310) at different time points. Each timepoint indicating one cycle of immunoadsorption.
Figure 2B:
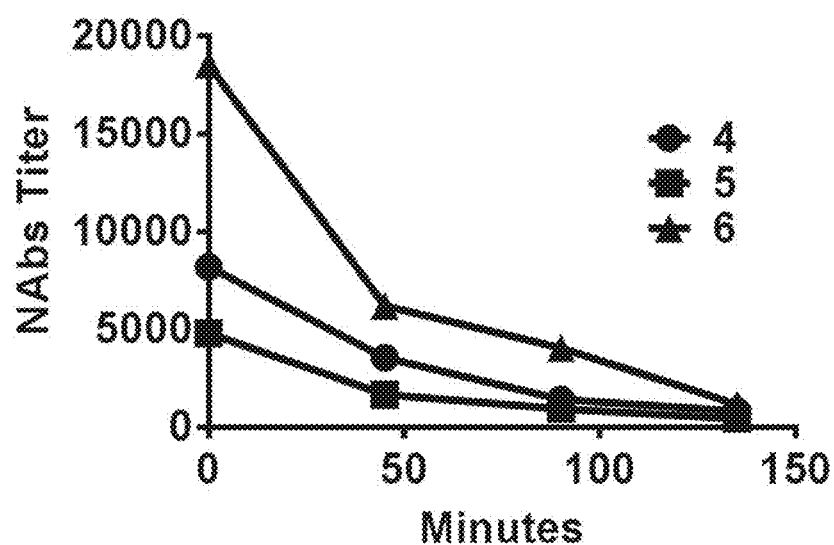
Figure 3:
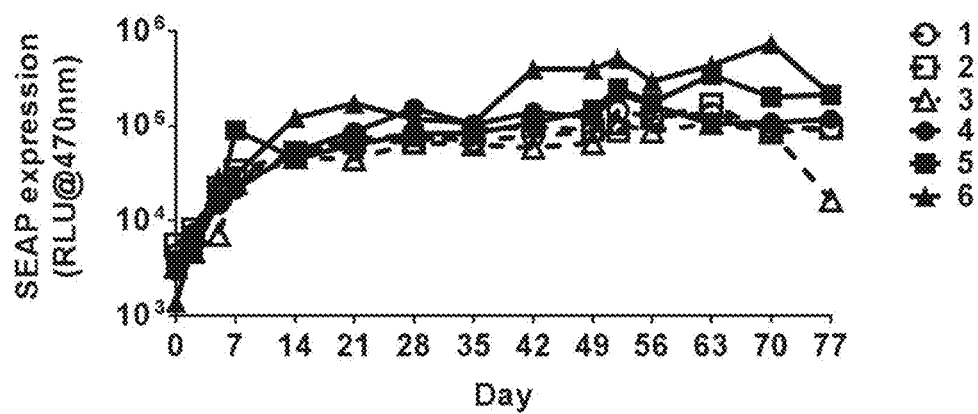
FIG. 3. SEAP expression in NHP. AAV5 SEAP was administered at day 0. AAV5 hFIX was administered at day 49.
Figure 4:
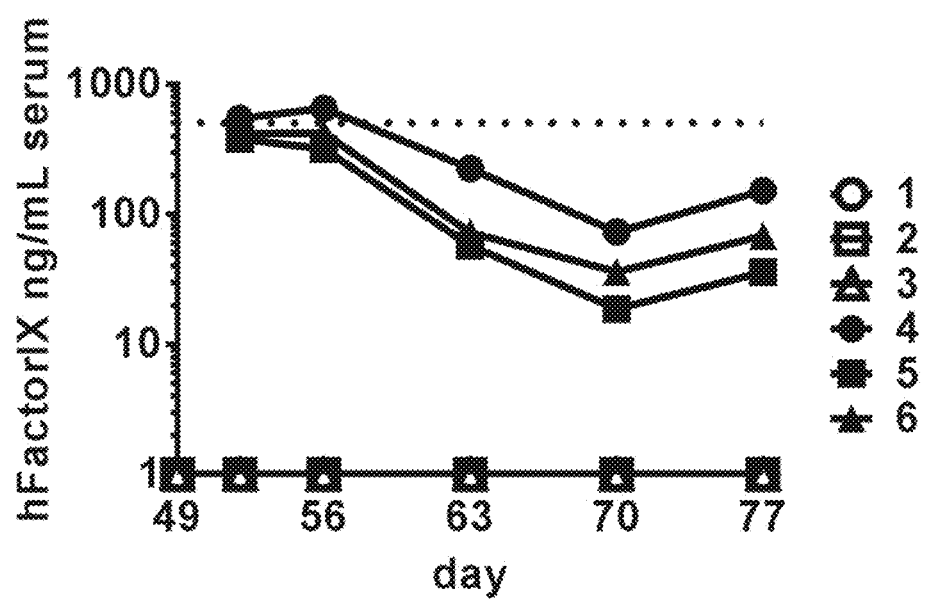
FIG. 4. human FIX expression in NHP. AAV5 hFIX was administered at day 49. No hFIX expression was detected in non-human primates that were not subjected to immunoadsorption. Initial hFIX expression levels were at the same level as observed in naïve non-human primates.

AAV neutralizing antibody titer and AAV binding antibody titer was measured in the NHP throughout the entire experiment. The AAV neutralizing antibody titer and AAV binding antibody titer were in the range as observed in naïve subjects having AAV administered. The immunoadsorption process strongly reduced the neutralizing antibody titer (FIGS. 2A-2B) in plasma. Importantly, after the second vector administration of AAV hFIX the animals that had received immunoadsorption showed high levels of hFIX expression around 7 days post administration. hFIX declined 20 days post administration and remained stable thereafter (FIG. 4). Such an expression profile in time has been described in previous NHP studies, also without prior exposure to AAV vectors and is independent of the serotype used. In contrast, the animals that did not receive immunoadsorption completely lacked any detectable hFIX expression at any time point. After the second administration a secondary response against AAV5 was observed by an increase in neutralizing antibody titre and AAV binding antibody titre. Combined, the results show that immunoadsorption resulted in a strongly reduced AAV neutralizing antibody titer in serum which provided for a time window that allows for highly efficient rAAV transduction.

Furthermore, measurements of Ig, IgM and IgG1 in the NHP related to NAb and TAb assays. This confirms that commercially available assays that are available for human Ig, IgM and/or IgG1 measurements may be used in a clinical setting to control the immunoadsorption and re-administration procedure. Such assays allow to determine the number of cycles required (by measuring immunoglobulin level before the immunoadsorption procedure), and/or allow to determine whether the desired reduction in immunoglobulin concentration has been achieved (by measuring the concentration shortly after the immunoadsorption procedure). Hence, the immunoadsorption procedure can be adapted (e.g. determining the number of cycles required) depending on immunoglobulin measurements in human subjects to ensure successful re-administration. This may allow for a well-controlled procedure wherein both the immunoadsorption and re-administration are performed on the same day.

The invention claimed is:

1. A method of administering a recombinant adeno-associated virus (rAAV) to a subject, comprising:
    (a) depleting a subject's circulating immunoglobulins by contacting the subject's blood with an extracorporeal device for immunoadsorption, the device comprising a binding moiety attached to a matrix, wherein the binding moiety binds immunoglobulins, and
    (b) subsequently administering a rAAV to the subject, wherein prior to depleting the subject's circulating immunoglobulins, the subject had neutralizing antibodies that bind to a capsid of the rAAV as a result of previously receiving a treatment comprising a rAAV vector.

2. The method of claim 1, wherein the binding moiety is selective for one or more of IgA, IgD, IgE, IgG and/or IgM.

3. The method of claim 1, wherein the binding moiety is selected from the group consisting of peptides, dextran sulfate, tryptophan, protein A, protein G, protein A/G, protein L, and anti-human immunoglobulin antibodies.

4. The method of claim 1, wherein the binding moiety comprises a protein that binds anti-rAAV immunoglobulins.

5. The method of claim 4, wherein the protein that binds anti-rAAV immunoglobulins binds to AAV VP1, AAV VP2, or AAV VP3.

6. The method of claim 1, wherein the rAAV is administered intravenously.

7. A method of decreasing a humoral immune response in response to a recombinant adeno-associated virus (rAAV) gene therapy in a subject comprising,
    (a) a first immunoadsorption step comprising contacting the subject's blood with a first extracorporeal device comprising a binding moiety that binds immunoglobulins, wherein the binding moiety is attached to a matrix,
    (b) a second immunoadsorption step comprising contacting the subject's blood with a second extracorporeal device comprising a binding moiety that binds anti-rAAV immunoglobulins, wherein the binding moiety is attached to a matrix, and
    (c) subsequently administering rAAV gene therapy to the subject, thereby decreasing the humoral immune response to the rAAV gene therapy;
    wherein prior to depleting the subject's circulating immunoglobulins, the subject had neutralizing antibodies that bind to a capsid of the rAAV as a result of previously receiving a treatment comprising a rAAV vector.

8. The method of claim 7, wherein the rAAV is administered intravenously.

9. The method of claim 7, wherein the first and second immunoadsorption steps depletes the amount of neutralizing antibodies in the subject's blood by at least 90%.

10. The method of claim 7, wherein the first and second immunoadsorption steps are performed at most 24 hours prior to administration of the rAAV.

11. The method of claim 7, wherein the subject is administered a dose of rAAV that is the same as a dose for a subject not having neutralizing antibodies for a capsid of the rAAV.

12. The method of claim 7, wherein a cellular response the rAAV is reduced.

13. A method for reducing an anti-rAAV immunoglobulin concentration in the blood of a subject, comprising:
    a) obtaining blood from the subject, wherein the subject's blood comprises neutralizing antibodies that bind to a capsid of the rAAV as a result of previously receiving a treatment comprising a rAAV vector;
    b) separating the blood into plasma components and cellular components;
    c) contacting the plasma components with an extracorporeal immunoadsorption device, the device comprising a binding moiety attached to a matrix, wherein the binding moiety binds anti-rAAV immunoglobulins;
    d) reconstituting the blood by combining the cellular components with the plasma components that were subjected to immunoadsorption; and e) administering the reconstituted blood to the subject, thereby reducing the anti-rAAV immunoglobulin concentration in the subject's blood.

14. The method of claim 13, further comprising administering an rAAV vector to the subject.

15. The method of claim 14, wherein the rAAV vector is administered to the subject within 24 hours of administering the reconstituted blood to the subject.

16. The method of claim 13, wherein the anti-rAAV immunoglobulin concentration in the subject's blood is depleted by at least 90%.

* * * * *